United States Patent [19]

Lehmann et al.

[11] Patent Number: 5,128,514
[45] Date of Patent: Jul. 7, 1992

[54] BLACK RADIATOR FOR USE AS AN EMITTER IN CALIBRATABLE GAS SENSORS

[75] Inventors: Volker Lehmann; Helmut Foell, both of Munich, Fed. Rep. of Germany

[73] Assignee: Siemens Aktiengesellschaft, Berlin and Munich, Fed. Rep. of Germany

[21] Appl. No.: 212,799

[22] Filed: Jun. 29, 1988

[30] Foreign Application Priority Data

Jul. 31, 1987 [DE] Fed. Rep. of Germany ....... 3725501

[51] Int. Cl.⁵ ............................................. H05B 3/28
[52] U.S. Cl. .................................. 219/209; 219/553; 250/493.1; 392/432
[58] Field of Search ................ 338/306, 307, 308-314, 338/22 SD, 22 R, 23, 34; 204/424, 425, 426; 219/209, 210, 543, 354, 345, 552, 553; 250/493.1, 504 R; 29/610.1, 611; 357/51; 73/27 R; 422/98; 392/432, 433

[56] References Cited

U.S. PATENT DOCUMENTS

| | | | |
|---|---|---|---|
| 2,152,934 | 4/1939 | Trent | 219/354 |
| 3,102,201 | 8/1963 | Braunstein et al. | 250/504 |
| 3,875,413 | 4/1975 | Bridgham | 219/354 |
| 4,338,281 | 7/1982 | Treitinger et al. | 422/98 |
| 4,389,876 | 6/1983 | Szonntagh | 73/27 R |
| 4,539,431 | 9/1985 | Moddel et al. | 219/354 |
| 4,644,141 | 2/1987 | Hagen et al. | 250/493.1 |
| 4,754,141 | 6/1988 | Mindock | 250/493.1 |
| 4,792,840 | 12/1988 | Nadd | 357/51 |
| 4,820,929 | 4/1989 | Modisette et al. | 250/504 R |
| 4,859,858 | 8/1989 | Knodle et al. | 250/504 R |
| 4,868,537 | 9/1989 | Blanchard | 338/309 |

FOREIGN PATENT DOCUMENTS

| | | |
|---|---|---|
| 0177724 | 8/1985 | European Pat. Off. |
| 1123841 | 2/1962 | Fed. Rep. of Germany |
| 3324232 | 7/1983 | Fed. Rep. of Germany |
| 3527857 | 2/1987 | Fed. Rep. of Germany |
| 137011 | 6/1978 | German Democratic Rep. |
| 151093 | 10/1979 | German Democratic Rep. |

*Primary Examiner*—Geoffrey S. Evans
*Attorney, Agent, or Firm*—Hill, Van Santen, Steadman & Simpson

[57] ABSTRACT

The black radiator contains a doped, crystalline silicon member having a honeycombed surface and contains a controllable electrical heating mechanism with which the silicon member can be heated. The heating mechanism has a heating coil that is a doped silicon structure that is oppositely doped to the doping of the silicon member and to which a controllable voltage is applied. The manufacturing method provides that the silicon member having a honeycombed surface be manufactured from an n-silicon member by electrolytic etching.

6 Claims, 1 Drawing Sheet

BLACK RADIATOR FOR USE AS AN EMITTER IN CALIBRATABLE GAS SENSORS

BACKGROUND OF THE INVENTION

The present invention is directed to a black radiator having adjustable temperature for use as an emitter in calibratable gas sensors.

SUMMARY OF THE INVENTION

An object of the present invention is to provide an optimally ideal, black radiator that is cost effective to manufacture and whose temperature can be simply adjusted and that can be used as an emitter in calibratable gas sensors.

In order to achieve this object, a black radiator of the type initially cited is characterized by:
a) a doped, crystalline silicon member having a honeycomb surface; and
b) a controllable, electric heater mechanism with which the silicon member can be heated.

An especially advantageous form of the invention includes a heater mechanism having a heating coil that is manufactured as a silicon structure in the silicon member. This silicon structure is oppositely doped from the doping of the silicon member and has a controllable voltage applied to it.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures in which like reference numerals identify like elements, and in which:

DESCRIPTION OF THE PREFERRED EMBODIMENT

Figure 1:
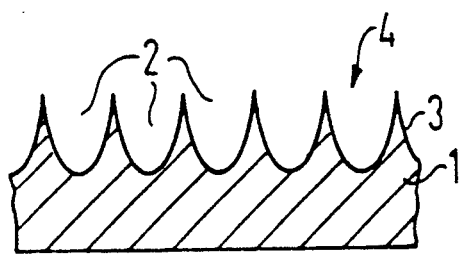
FIG. 1 is a cross-sectional schematic illustration of a silicon member having a honeycombed surface.

The honeycombed surface shown in FIG. 1 is produced by electrolytic etching of a crystalline, n-doped silicon piece or member 1. The honeycomb size and, thus, the emission can be optimized by variation of the etching parameters. The honeycomb cells 2 have a width and depth of about 10 through 20 $\mu$m and the walls 3 have a thickness of about 2 through 5 $\mu$m. The silicon piece 1 represents an extremely good black radiator. For light incidence on the honeycombed surface 4, a multiple reflection occurs inside the honeycomb cells 2 and, as a result thereof a nearly total absorption of light at all wavelengths occurs.

Figure 2:
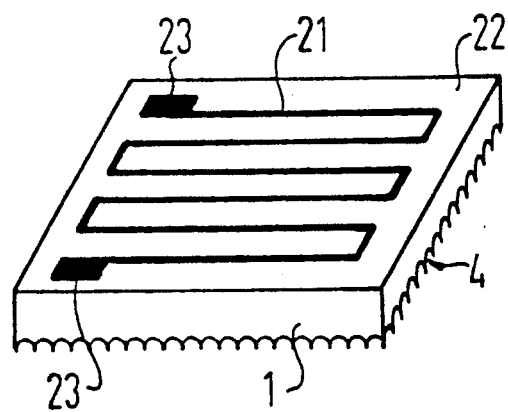
FIG. 2 is a perspective view of a black radiator of the present invention.

As shown in FIG. 2, a p-doped, meandering-shaped silicon structure 21 is formed as a heating coil in the n-silicon piece 1 by depositing dopants, for example boron. The heating coil is connected to a controllable constant voltage (not shown in the illustration) via the electrical terminals 23. One surface 4 of the n-silicon piece 1 is provided with a honeycombed structure. When an electrical current flows in the p-doped silicon structure 21, the n-silicon piece 1 heats up. The honeycombed surface 4 then emits a radiation as is characteristic of black radiators. The temperature of the n-silicon piece and, thus, the radiation density can be set by controlling the current flow.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. A black radiator having adjustable temperature for use as an emitter in calibratable gas sensors, comprising:
   a) a doped, crystalline silicon member having a honeycombed surface on a first side that emits radiation as a function of a temperature level of the silicon member; and
   b) a controllable electrical heating mechanism on a second side of the silicon member with which said silicon member can be heated.

2. A black radiator having adjustable temperature for use as an emitter in calibratable gas sensors, comprising:
   a) a doped, crystalline silicon member having a honeycombed surface on a first side, and
   b) a controllable electrical heating mechanism on a second side of said silicon member with which said silicon member can be heated, the heating mechanism being a heating coil that is manufactured as a doped silicon structure in said silicon member and that is oppositely doped to the doping of the silicon member and to which a controllable voltage is connected.

3. The black radiator according to claim 2, wherein the heating mechanism is applied to a surface lying opposite the honeycombed surface.

4. The black radiator according to claim 2, wherein the honeycombed surface is produced by electrolytic etching.

5. A black radiator having an adjustable temperature for use as an emitter in calibratable gas sensors, comprising:
   a doped, crystalline silicon member having a honeycombed surface on a first side, said silicon member having a first doping; and
   at least one meandering-shaped heating coil on a second side, opposed to said first side, of said silicon member, said heating coil being a doped silicon structure in said second side of said silicon member, said doping of said second side being opposite to said doping of said silicon member;
   wherein said heating coil has at least two terminals.

6. The black radiator according to claim 5, wherein the honeycombed surface is produced by electrolytic etching.

* * * * *